United States Patent [19]
Ishida

[11] Patent Number: 5,262,070
[45] Date of Patent: Nov. 16, 1993

[54] METHOD, APPARATUS AND ASSOCIATED ATTACHMENT FOR LIQUID COMPONENTS SEPARATION

[75] Inventor: Noboru Ishida, Fujinomiya, Japan

[73] Assignee: Terumo Kabushiki Kaisha, Tokyo, Japan

[21] Appl. No.: 745,227

[22] Filed: Aug. 14, 1991

[30] Foreign Application Priority Data

Aug. 17, 1990 [JP] Japan ................ 2-216667

[51] Int. Cl.⁵ .............................................. B01D 17/02
[52] U.S. Cl. ...................................... 210/800; 100/35;
 100/211; 210/513; 210/767; 222/95; 383/906;
 604/408
[58] Field of Search ............... 210/789, 767, 513, 800;
 604/403, 408, 410; 383/906; 222/94, 95, 103,
 105, 96; 100/35, 110, 211

[56] References Cited

U.S. PATENT DOCUMENTS

| | | | |
|---|---|---|---|
| 3,687,131 | 8/1972 | Rayport et al. | 606/157 |
| 4,310,955 | 1/1982 | Davis | 24/248 |
| 4,413,771 | 11/1983 | Rohde et al. | 604/410 |
| 4,463,876 | 8/1984 | Swallert | 222/94 |
| 4,482,342 | 11/1984 | Lueptow et al. | 604/410 |
| 4,857,190 | 8/1989 | Wada et al. | 210/534 |
| 4,892,537 | 1/1990 | Carmen et al. | 604/408 |
| 4,969,882 | 11/1990 | Carmen et al. | 604/410 |
| 4,976,851 | 12/1990 | Tanokura et al. | 222/103 |
| 5,045,185 | 9/1991 | Ohnaka et al. | 222/103 |
| 5,071,570 | 12/1991 | Shiraki et al. | 210/789 |
| 5,135,646 | 8/1992 | Tanokura et al. | 222/103 |

FOREIGN PATENT DOCUMENTS

| | | |
|---|---|---|
| 167682 | 5/1956 | Australia . |
| 216280 | 12/1956 | Australia . |
| 254544 | 9/1964 | Australia . |
| 1-53811/79 | 7/1980 | Australia . |
| 0191360 | 8/1986 | European Pat. Off. . |
| 791908 | 12/1935 | France . |
| 2599837 | 12/1987 | France ................ 604/403 |
| 662737 | 10/1987 | Switzerland ........ 604/403 |

*Primary Examiner*—Joseph W. Drodge
*Attorney, Agent, or Firm*—Frishauf, Holtz, Goodman & Woodward

[57] ABSTRACT

A method for separating liquid components which have been fractionated into at least an upper layer component and a lower layer component in a soft flexible container provided with a liquid transfer port located either at an upper part or a lower part of the container comprising a step of pressing the container to a flat configuration, so as to flowing out one of the liquid components through the liquid transfer port, characterized in that the inner walls of a liquid storage chamber of the flexible container, except for the liquid transfer port, are partly brought into close contact with each other in advance, so as to define such a flowing passage for the liquid component, the width of which becoming narrower toward the liquid transfer port, prior to the step of pressing the flexible container to a flat configuration.

19 Claims, 13 Drawing Sheets

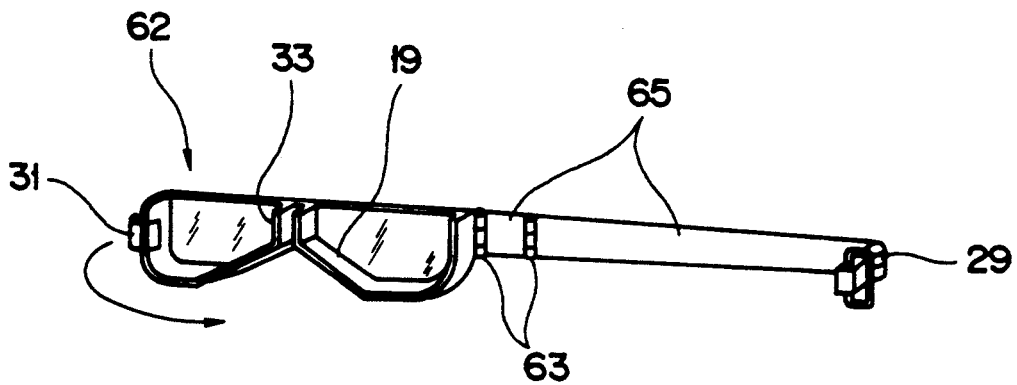
F I G. 13 A
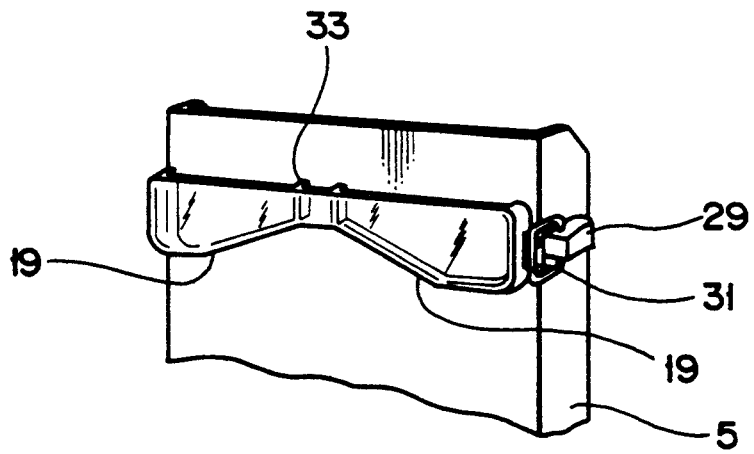
F I G. 13 B

METHOD, APPARATUS AND ASSOCIATED ATTACHMENT FOR LIQUID COMPONENTS SEPARATION

BACKGROUND OF THE INVENTION

1. Field of the Invention

The present invention relates to a method for separating blood components, for example, plasma, platelet and erythrocyte, from whole blood contained in a flexible container such as a blood bag or the like, and also to an apparatus and an associated attachment, which is contrived for use in the method referred to above.

2. Description of the Related Art

Recently, it has been recognized that whole blood transfusions cause undesired effects on a patient. Therefore, in view of alleviating certain physiological burdens, and suppressing the side effects due to immune reaction, such a mode of transfusion is widely applied today, wherein only the blood component or components which the patient requires is transfused into a blood circulatory system of the patient.

To obtain blood component preparations, it is necessary to fractionate the whole blood collected in a master blood bag (donor bag) into respective components by using a centrifugal separator, and to separate the components by transferring each component into an individual sub-bag from the master bag.

To meet this requirement, the prior art uses such a separator 71 as illustrated in FIG. 1, wherein the blood components in the master bag 73, i.e. an upper layer comprising plasma, and a middle layer otherwise called a buffy coat (comprised mainly of leukocytes, and partly of platelets, erythrocytes and plasma mixed therein) which have been centrifugally fractionated from the whole blood, are separately transferred into their sub-bags manually, and then sealed with a blockade provided in a connecting tube leading to each sub-bag, using a tube sealer.

More specifically, the master blood bag 73 which has been subjected to centrifugal separation is first set on suspender pins 75 of said separator, with care not to stir up the blood cells in said master blood bag.

FIG. 2A shows how the master blood bag is set in that position, wherein 77 denotes plasma, 79 a buffy coat, and 81 dense erythrocytes.

Next, the master blood bag 73 is held between a retainer plate 87 (FIG. 1) of the separator 71, and a pressurizing plate 89 which swings via a lever 83 to which certain force is applied constantly in a given direction from a spring (not shown), with the lever 83 of the separator 71 disengaged from the hook 85 held on a base 84, whereby a plasma component 77 constituting the upper layer may be transferred into a first sub-bag (not shown) from the master blood bag 73 through a liquid transfer port 74.

FIG. 2B illustrates the condition of the master blood bag at an above-mentioned stage of transfer.

Then, the plasma component still remaining in the master bag 73, the buffy coat and a part of the erythrocytes component are transferred into a second sub-bag (not shown) through repetitions of the procedure similar to the above.

FIG. 2C represents a post-transfer condition of the master blood bag 73 after the transfer of blood components has been completed.

In the prior art, the transfer of blood components is carried out in the above-described manner, from the master blood bag in which the whole blood is first gathered, into respective sub-bags.

However, it must be noted that the prior art wherein said separator 71 is used for the transfer of blood components is confronted with such a problem giving rise to an inconvenience that the leukocytes and platelets which are respective components constituting the buffy coat, get into each liquid drain port 91 provided at the upper portion of the master bag 73 by accident.

Normally, these blood components must be transferred into the second sub-bag.

Such an inconvenience would result in that the dense erythrocytes left as the lowermost layer in the master blood bag 73, which is due to be recovered, would sometimes undergo accidental mixing with the leukocytes and platelets, with a consequential problem thereby caused, entailing an inconvenience that there would be insufficiency of removing the leukocytes, etc. from the dense erythrocytes. Further, when the platelets are recovered from the buffy coat previously transferred into the second sub-bag, it gives rise to another problem of being a low recovery with the platelets because a part of the buffy coat remains in the master bag 73.

In order to solve these problems, it has been proposed that, as shown in FIG. 3, a shoulder part 93 of the master blood bag 73 be so formed with an acute angle of $\theta$ defined as being approximately 18° against the horizontal line, whereby a downward shoulder line might be provided, thereby increasing the flow rate of each blood component running through the liquid transfer port 74 so that no buffy coat would flow into each liquid drain port 91. Regrettably, however, such a proposal failed to sufficiently eliminate the problems mentioned above.

SUMMARY OF THE INVENTION

It is, therefore, an object of the present invention to provide a method and an apparatus for allowing to separate liquid components with high separation accuracy by preventing different liquid components from accidental mixing, in a step of separating liquid components such as blood components.

In order to achieve the object, a first aspect of the present invention provides a method for separating liquid components, comprising a step wherein the separation of liquid components having been fractionated into at least an upper layer and a lower layer in a soft flexible container which has a liquid transfer port located either at an upper part or a lower part of the container is carried out by pressing the container to a flat configuration, so as to flowing out one of the liquid components through the liquid transfer port, characterized in that the inner wall of a liquid storage chamber of the flexible container, except for the liquid transfer port, is partly brought into close contact with each other in advance so as to define such a dischaging passage, the width of which will become narrower toward the liquid transfer port, prior to a step of separating the liquid component on the side of the liquid transfer port by pressing the flexible container to a flat configuration.

Further, a second aspect of the present invention provides an apparatus which is directly used for carrying out the method of the present invention. The apparatus comprises a retaining means to hold slantingly or perpendicularly a flexible container having a liquid transfer port located either at an upper part or a lower part thereof, a pressurizing means arranged opposite to said retainer means, for enabling to hold the flexible container between the retaining means and the pressurizing means and to press the container into a flat configuration, and a squeezer means which is attached to the retaining means and arranged so as to be positioned over the liquid transfer port side of the flexible contain for, the squeezer means enabling to squeeze the liquid transfer port side of said flexible container held on the retaining means in such a manner that the inner wall of the liquid chamber, except for the liquid transfer port, may partly be brought into close contact with each other, thereby forming a passage for discharging the liquid component which becomes narrower toward the liquid transfer port.

Further, a third aspect of the present invention provides an associated attachment for direct use in carrying out the method of the present invention. The associated attachment is a squeezing tool comprising a squeezing member which is workable to bring respective inner wall of a soft flexible container, except for the liquid transfer port, into close contact with each other in such a manner that a passage may be formed, wherein the passage will becomes narrower toward the liquid transfer port.

The apparatus according to the present invention, which is contrived to separate liquid components one from another, is used as follows. First, a soft flexible container having a liquid transfer port located either at an upper part or a lower part thereof is set on a retaining means which is arranged slantingly or perpendicularly, the flexible container being filled with liquid which has been fractionated into layered components to be separated each other.

In the next step, the flexible container set in the position is sqeezed by using a squeezer means provided on the retaining means, the squeezer means is arranged on a liquid transfer port side of the retaining means. As a result, the liquid transfer port side of said flexible container is squeezed in such a manner that the respective inner wall of a liquid storage chamber may be partly brought into close contact with each other, except for the liquid transfer port of said flexible container. By the squeezing, a passage may be formed which will become narrower toward said liquid transfer port.

Successively, said flexible container is held between the retaining means and a pressurizing means, and is then externally pressed to a flat configuration by working of the pressurizing means.

Thus, one liquid layer component positioned on the liquid transfer port side, which is one of at least an upper and a lower component layers contained in the flexible container, is discharged through the liquid transfer port.

At this stage, the respective inner wall of the liquid storage chamber, except for the liquid transfer port of said flexible container, are already partly held in close contact with each other by using the squeezer means, in such a manner that a passage may be formed which will become narrower toward the liquid transfer port. Therefore, the liquid component layer on the liquid transfer port side runs along said passage, and flows out through the liquid transfer port, with the flow rate of the liquid component getting gradually accelerated as the liquid component approaches said liquid transfer port.

Since the passage for discharging the liquid component is so restricted as described above, the liquid component on the liquid transfer port side is assured free from accidentally getting into the liquid drain port and the like other than the liquid transfer port of said flexible container. As a result, the liquid component are smoothly flowed out and discharged, without staying or remaining in the master bag.

As a consequence with no liquid component remaining in the flexible container, high separability is obtainable and the recovering rate of a liquid component can be improved.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

Figure 1:
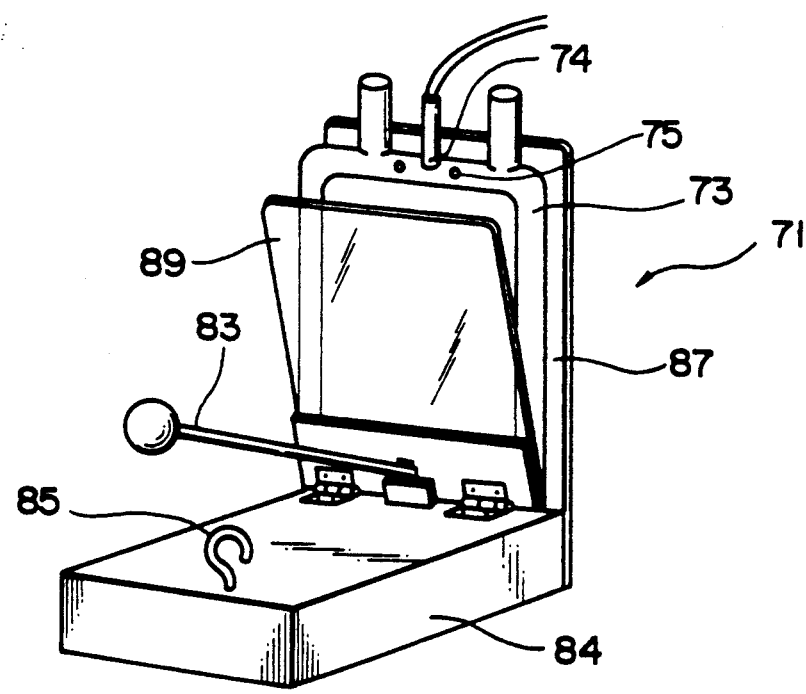
FIG. 1 illustrates a conventional liquid component separator.
Figure 3:
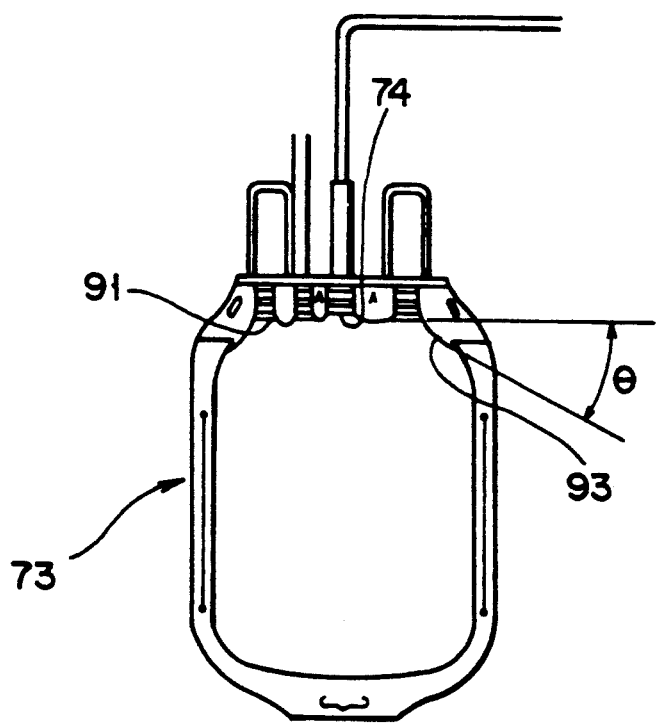
Figure 2:
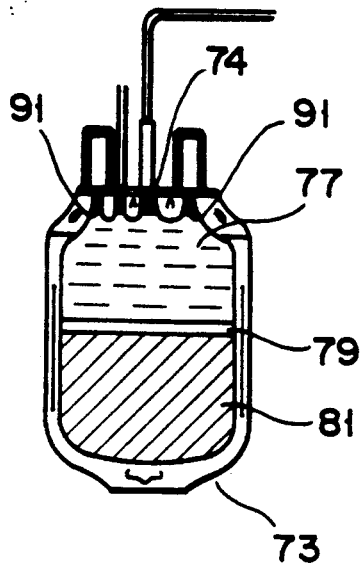
Figure 2:
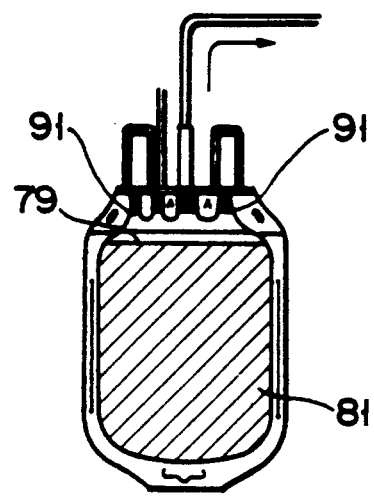
Figure 2:
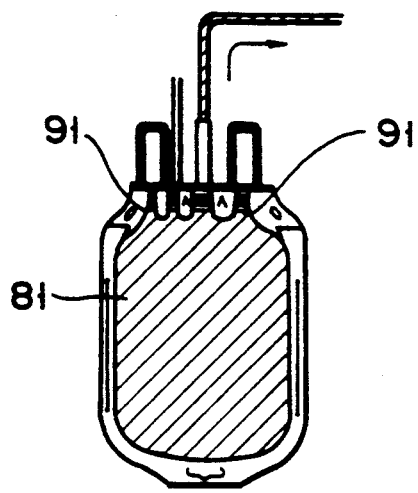
Figure 4:
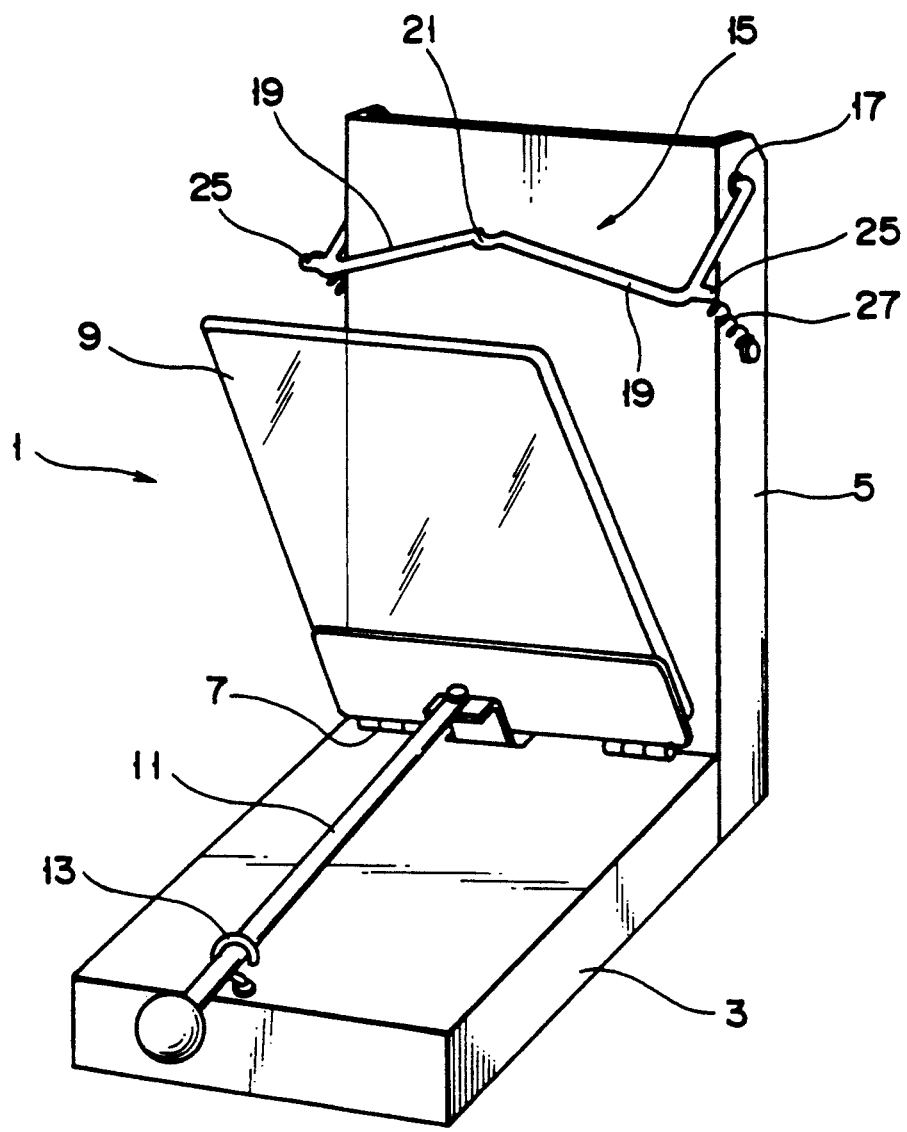
Figure 5:
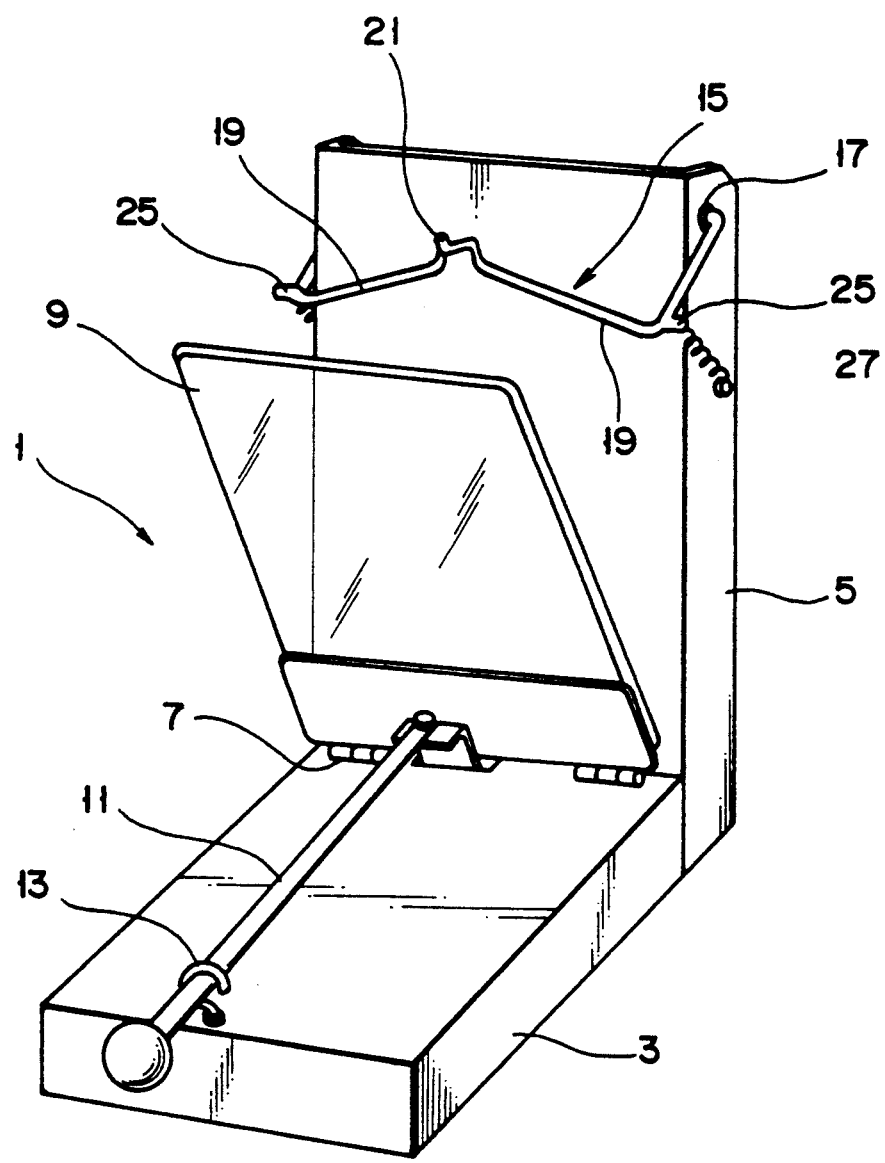
Figure 6A:
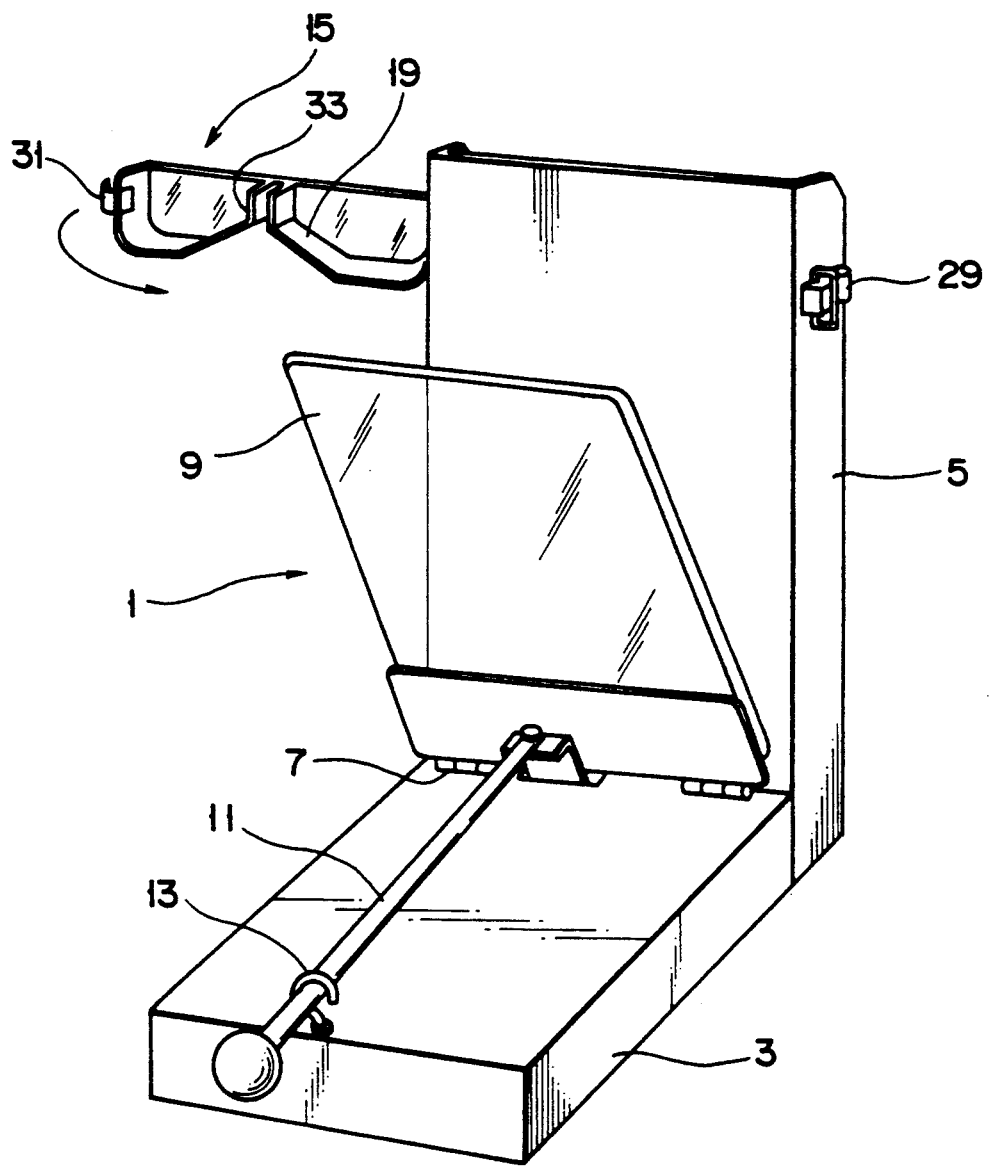
Figure 6B:
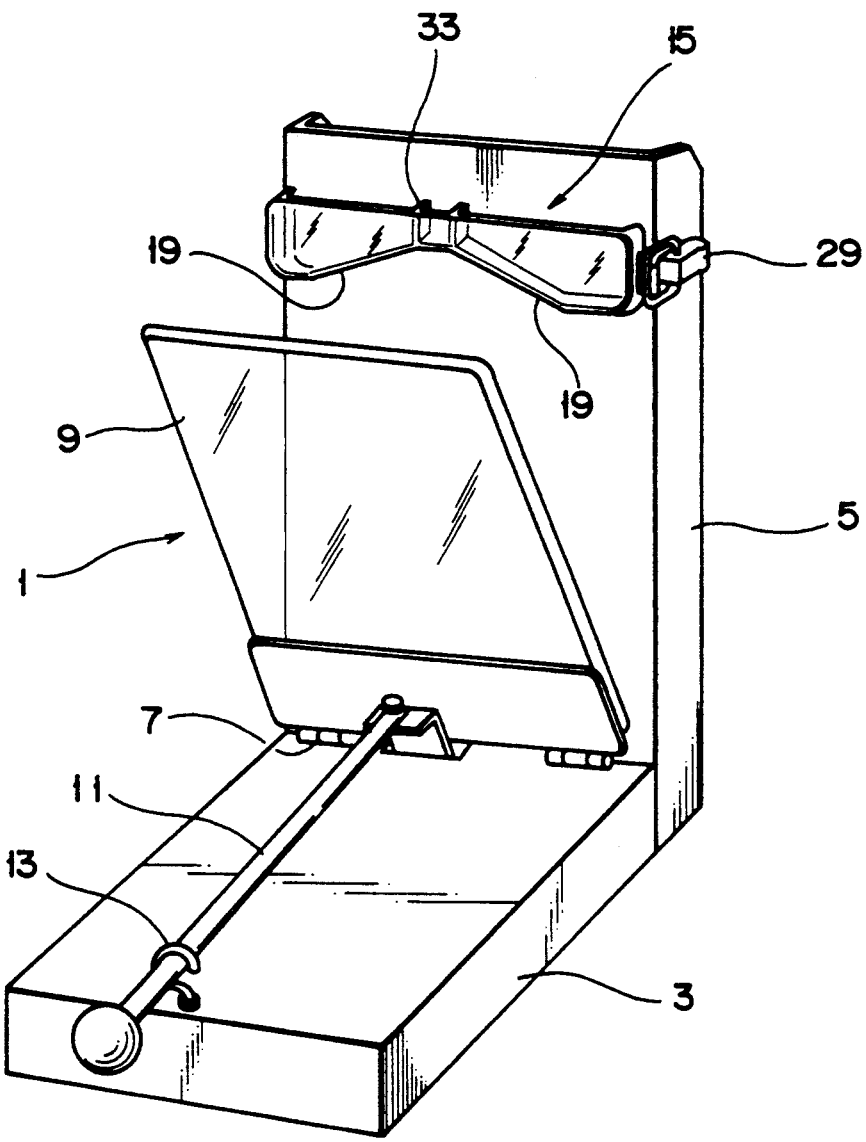
Figure 7:
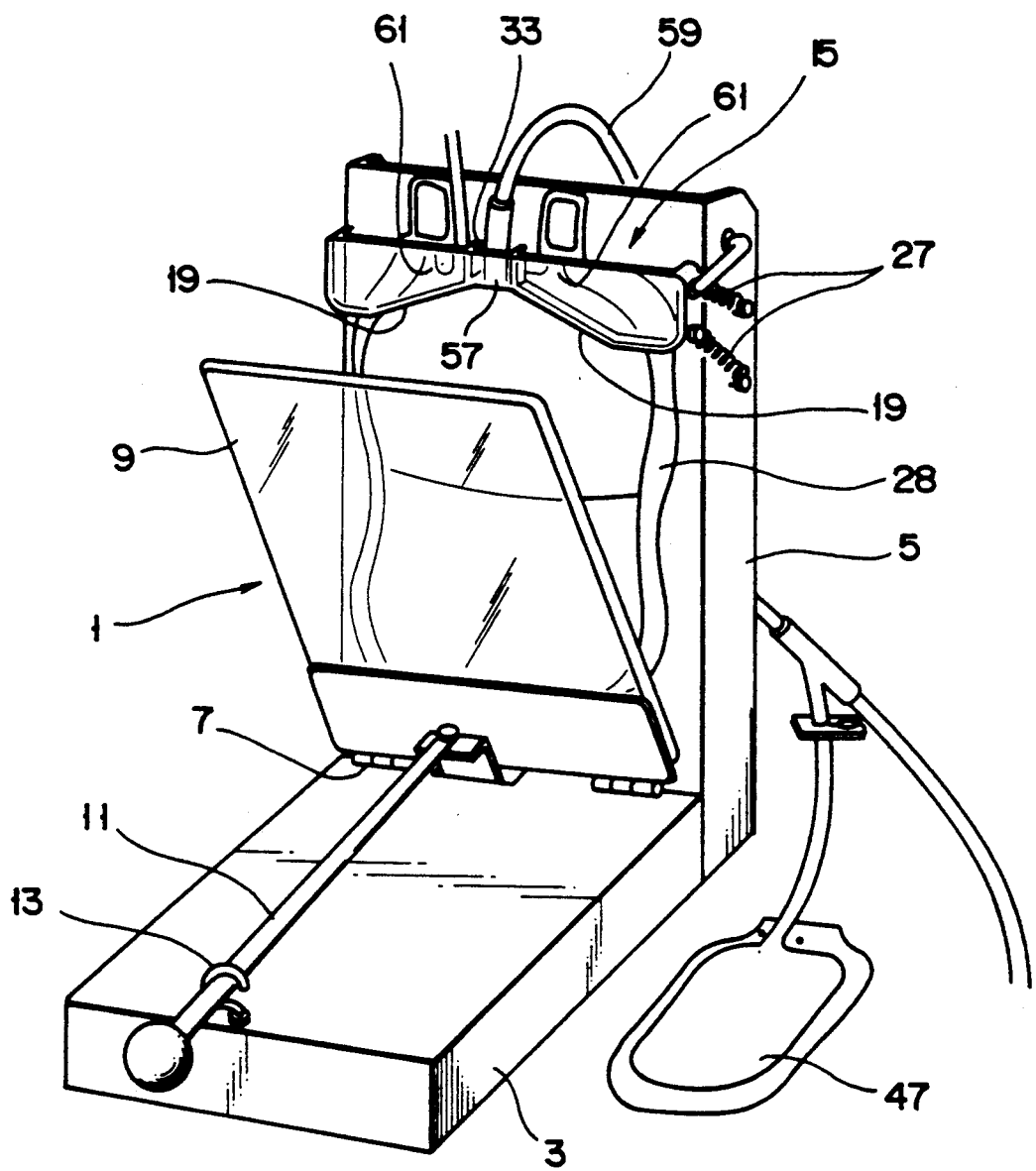
Figure 8:
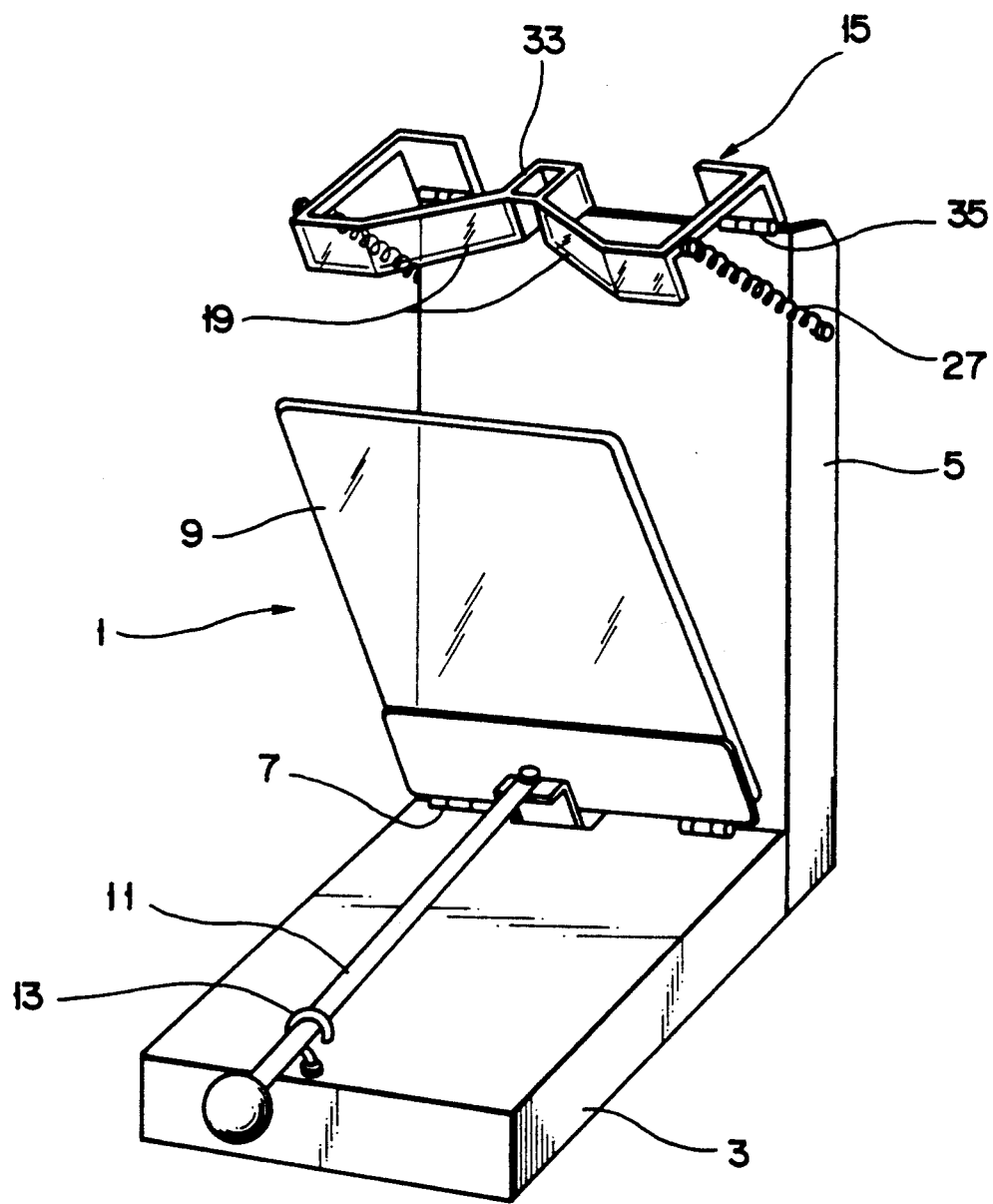
Figure 9:
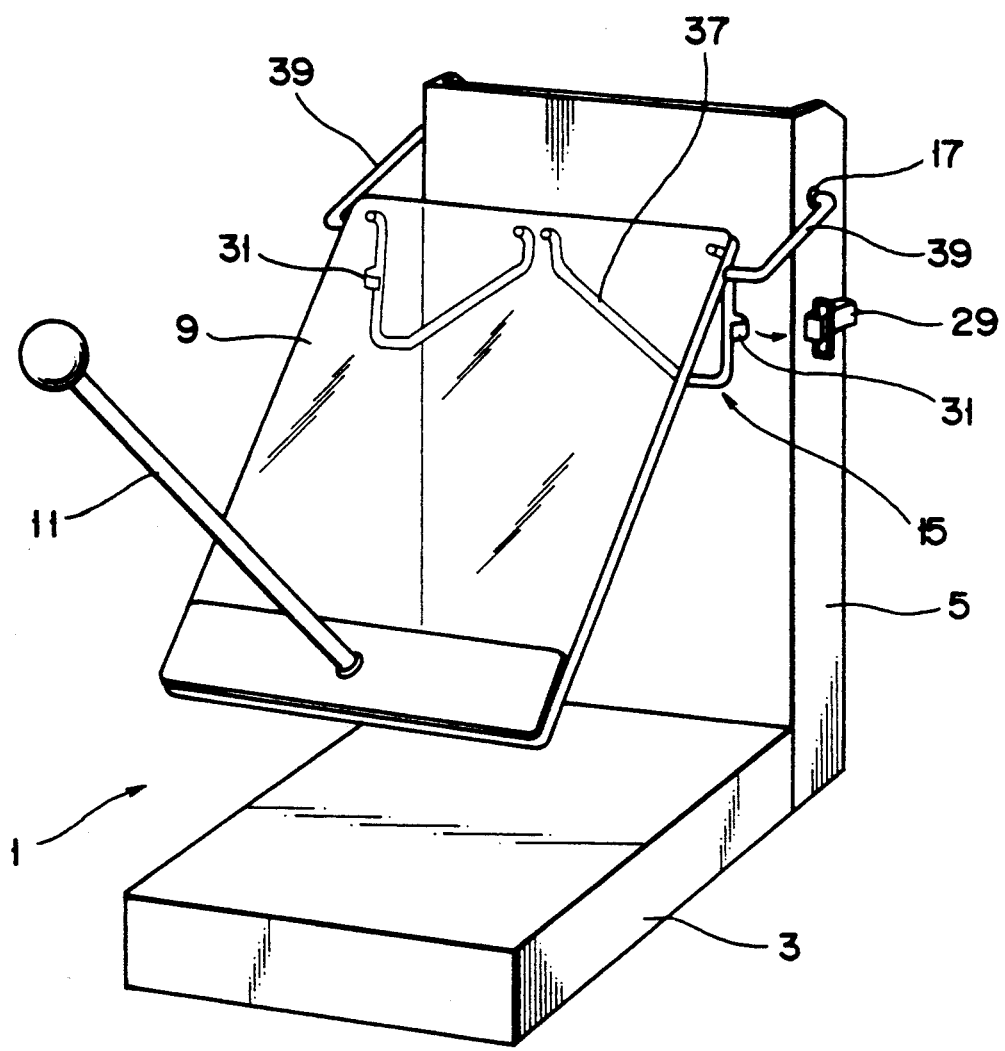
Figure 10:
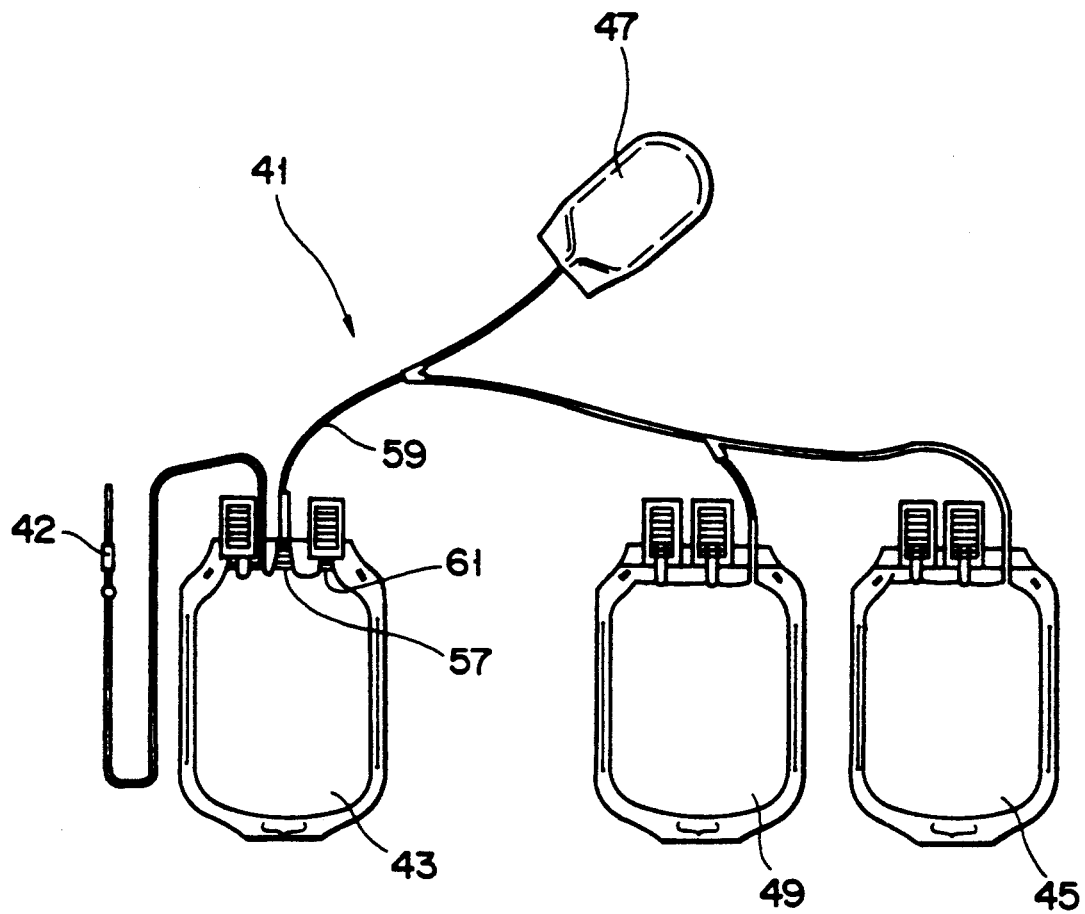
Figure 11A:
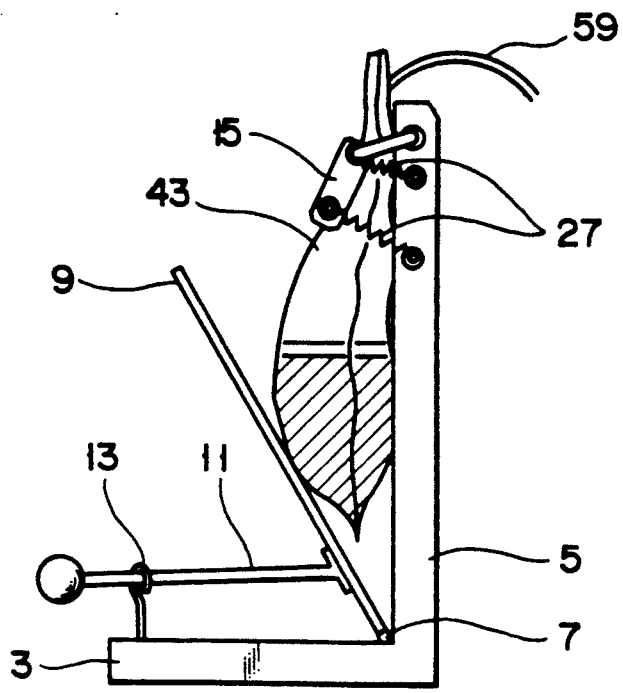
Figure 11B:
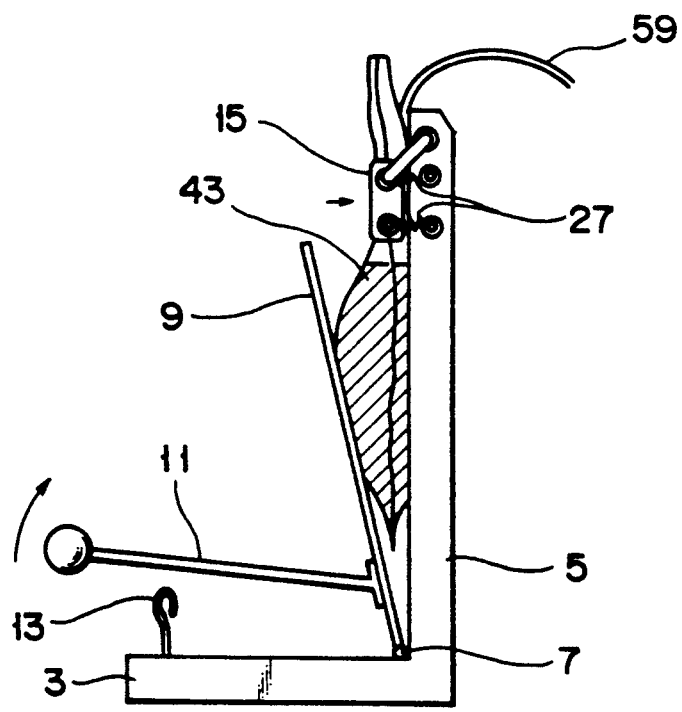

Each of FIGS. 2A, 2B and 2C is an illustrative diagram showing how each of the blood components is transferred to the exterior from the master blood bag in a case where the conventional blood component separator is used;

FIG. 3 is an illustrative diagram showing a master blood bag with downward shoulder portions;

FIG. 4 is a perspective view of the first preferred embodiment of a liquid component separator according to the present invention;

FIG. 5 is a perspective view of the second preferred embodiment of a liquid component separator according to the present invention;

Each of FIGS. 6A and 6B is a perspective view of the third preferred embodiment of a liquid component separator according to the present invention;

FIG. 7 is a perspective view of the fourth embodiment of a liquid component separator according to the present invention;

FIG. 8 is a perspective view of the fifth preferred embodiment of a liquid component separator according to the present invention;

FIG. 9 is a perspective view of the sixth preferred embodiment of a liquid component separator according to the present invention;

FIG. 10 is an illustrative diagram showing a blood bag comprising four bags;

Each of FIGS. 11A and 11B is an illustrative diagram showing how the liquid component separator of the present invention is applied;

Each of FIGS. 12A, 12B, 12C, and 12D is an illustrative diagram showing how each of the blood components is transferred to the exterior by pressing the master blood bag; and Each of FIGS. 13A and 13B is an illustrative diagram showing a squeezer means according to the present invention.

DETAILED DESCRIPTION OF THE PREFERRED EMBODIMENTS

The present invention is now described in detail, referring to one preferred embodiment of the present invention illustrated in the drawings.

FIG. 4 is an illustrative diagram showing the first preferred embodiment of a liquid component separator according the present invention.

With reference to FIG. 4, the liquid separator has a base plate 3 made of metal, etc, at the bottom thereof. At one end of the base plate 3, there is provided a retainer plate 5 made of a metal, etc. and which extends perpendicularly to hold a flexible container.

It is noted here that the retainer plate 5 may be provided in an inclined arrangement.

A pressurizing plate 9 is provided at a boundary between the base plate 3 and the retainer plate 5, which is swingably mounted with respective hinges duly arranged.

The pressurizing plate 9 is formed of a glass plate or a transparent plastic plate, and is constructed to press the flexible container held between the pressurizing plate 9 and the retainer plate 5 into a flat configuration.

At a lower end center of the pressurizing plate 9, there is provided a lever 11 which helps the operation of the pressurizing plate 5 for pressing the flexible container.

As illustrated in the figure, a hook 13 is mounted on the upper surface of the base plate 3 to lock the lever 11.

At the upper part of the retainer plate 5, there is arranged a squeezer means 15 which squeezes the liquid transfer port side of the flexible container set on the retainer plate 5, thereby bringing respective inner walls of a liquid storage chamber into close contact, except for the liquid transfer port, in such a manner that a passage may be formed, which will become narrower toward the liquid transfer port.

The squeezer means 15 is of a bar-like configuration made of a metal, etc. The squeezer means is in such work position that the left and right ends thereof are inserted into respective openings 17 provided at the upper left and right parts of said retainer plate 5, whereby said squeeze means 15 is swingable around these openings.

It is noted that the squeezer means 15 gives a symmetrical obtuse-angled roof configuration in a front view, wherein an obtuse angle is defined at less than 180°, with the left and right arm portions 19 symmetrically inclined downward.

At least the respective arm portions 19 may be formed, using a stainless steel wire, acrylonitrile styrene resin, rigid PVC, and the like.

It is further noted that the arm portions 19 formed of a transparent or semi-transparent plate results in not only enabling the arm portions to produce squeezing force but also rendering the arm portions to provide a clear view of the boundary between fractionated liquid component layers.

It is also noted that the obtuse angle defined between the respective arm portions 19 is desired within a range from 100° to 150°.

The obtuse angle defined beyond 150° entails a case wherein the arm portions contact an injection-molded portion such as the liquid transfer port at the upper part of the flexible container, whereby said arm portions are interfered with, sometimes failing to achieve sufficient squeezing. On the other hand, when the obtuse angle is defined at less than 100°, there is brought about such an inconvenience wherein the arm portions 19 will sometimes fail to obtain sufficient squeezing due to the volumetric pressure of a liquid contained in the flexible container.

At the center portion of the left and right arm portions 19, there is provided a bend portion 21 which projects in a direction of going away from the retainer plate 5 so that the liquid transfer port of the flexible container is assured free from being squeezed by the arm portions 19.

It is likewise noted that each of the left and right arm portions 19 is provided with a projection 25 which engages with one end of a spring 27, the opposite end of which is fixed to either the left or right side of the retainer plate 5. The spring 27 allows to apply its recovery force on the liquid storage chamber to squeeze same, except for the liquid transfer port, in a direction toward the retainer plate 5.

By such squeezing as described above, respective inner walls of the liquid storage chamber, except for the liquid transfer port, are brought into close contact with each other, whereby a passage is formed, which passage will become narrower toward the liquid transfer port.

Presented in FIG. 5 is the second preferred embodiment of a liquid component separator according to the present invention. The second embodiment differs from the first embodiment in respect that the position of the bend 21 is projected slightly up from the center of the arm portions 19.

With the bend 21 so situated as described above, it becomes possible not only to perpendicularly hold a cylindrical liquid transfer port of the flexible container, but also to effectively work the squeezer means 15, whereby the respective inner walls of the liquid storage chamber may be brought into perfectly close contact with each other.

Shown in each of FIGS. 6A and 6B is the third preferred embodiment of a liquid component separator according to the present invention. A difference between the third embodiment and the second embodiments lies in a goggle-like configuration of the squeezer means 15. Another difference lies in that the left end of one arm portion 19 is swingably fixed by means of a hinge onto the left side of the retainer plate 5, as well as a hook 31 is provided at the right end of another arm portion 19, which hook is engageable with a lock 29 arranged at the right side of the retainer plate 5.

FIG. 6A illustrates a state prior to the engagement between the lock 29 and hook 31, while illustrated in FIG. 6B is a post-engagement state wherein the lock 29 and hook 31 are engaged with one another.

It is noted that at the central part of the left and right arm portions 19, there is provided a spacer means 33, within which the cylindrical liquid transfer port of the flexible container is held, whereby the liquid transfer port is ensured free from being squeezed.

Presented in FIG. 7 is the fourth embodiment of a liquid component separator according to the present invention. The fourth embodiment is different form the third embodiment in that the former is not provided with lock 29 and hook 31, but provided instead with the spring 27 similarly to the first and second embodiments.

It is noted here that a rubber-like elastic member and the like may be used in place of the spring 27.

Illustrated in FIG. 7 is a state wherein the flexible container 28 is squeezed and locked by the squeezer means 15.

FIG. 8 shows the fifth embodiment of the liquid component separator according to the present invention. The major points over which the fifth embodiment differs from the fourth embodiment is that the squeezer means 15 is swingably coupled to the upper end of the retainer plate 5 via hinges 35.

FIG. 9 illustrates the sixth embodiment of a liquid component separator according to the present invention.

The sixth embodiment is so configured, as shown in the figure, that the squeezer means 15 comprises a pair of angled bar-like members 37 made of a metal, etc., wherein each of said angled bar-like member has upper end coupled to an upper portion of a pressurizing plate 9 at a given angle provided between said pressurizing plate and said bar-like members.

In addition, a pair of link bars 39, one extending left from the upper part of the pressurizing plate 9 and another extending right, are so provided that their one ends inserted and held in respective openings 17 provided at the upper left and right side of the retainer plate 5, whereby the link bars 39 becomes swingable around these openings 17.

Each of the angled bar-like members 37 is provided with a hook 31 which is located on the left or right side of the bar-like member respectively, whereby these hooks 31 becomes engageable with the respective locks 29 arranged at the left and right sides of the retainer plate 5.

The sixth embodiment has such a configuration wherein the pressurizing plate 9 swings around its upper end, whereby an upper part pressurizing system is defined in the present embodiment, while each of the preceding embodiments employs a lower part pressurizing system.

When the liquid components are transferred via the liquid transfer port from the interior of the flexible container by means of the upper part pressurizing system, the flow rate of a liquid component at which the components runs through a narrow cross-sectional area in the upper part of the flexible container is accelerated according to the fluid continuity principle.

This results in lessening the possibility of occurring the problem that the liquid component to be transferred exterior are partly stayed or remained at the upper part of the flexible container due to failing to flow out.

The method of using the liquid component separator according to the present invention is described below with reference to the fourth embodiment.

Prior to applying the liquid component separator, four inter-coupled blood bags 41 are prepared as respective flexible containers, as shown in FIG. 10.

The blood bags 41 comprises a blood collector needle 42, a master bag 43, a first sub-bag 45, a second sub-bag 47, and a third sub-bag 49 which are coupled together with connecting tubes and branched tubes.

Then, via the blood collector needle 42, 400 ml of blood is collected into the master bag 43 from a blood donor.

Successively, the blood collected in the master bag is subjected to centrifugal separation which is effected at a speed of 3,500 rpm for a period of 6 minutes.

Through the centrifugal separation, the blood in the master bag is fractionated into an upper layer which is a plasma component, a middle layer which is a buffy coat component (comprising mostly of leukocytes, and partly of platelets, erythrocytes and plasma), and a lower layer which is a dense erythrocytes component.

Thereafter, the arm portions 19 of the squeezer means 15 of the liquid component separator are raised off from the surface of the retainer plate 5, resisting against the force of each spring 27, and master bag 43 is then set to the liquid component separator of the present invention, exercising care so as to prevent upper middle and lower layers of the blood in the master bag from being mixed up. FIG. 7 shows how the master bag is set to the liquid component separator according to the present invention.

Presented in FIG. 11A is a right side view of the master bag 43 duly set to the liquid component separator shown in FIG. 7.

FIGS. 12A through 12D show how each of the upper, middle and lower layer of the blood in the master bag—which is set to the liquid component separator—is transferred to the exterior, as the process of pressing progresses. For the convenience of a simplified illustration, only the arm portions 19 of the squeezer means 15 and the spacer means 33 are represented with the other parts being omitted.

Figure 12A:
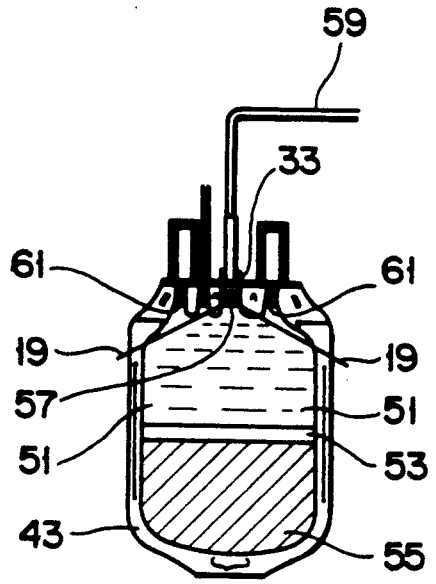

More specifically, FIG. 12A is an illustrative diagram showing the duly set master bag 43 which is immediately after the centrifugal separation, wherein 51 denotes an upper layer comprising a plasma component, 53 a middle layer comprising a buffy coat component, and 55 a lower layer made up of a dense erythrocytes component.

In a subsequent step, as shown in FIG. 11B, the lever 11 is disengaged from the hook 13 and raised to swing the pressurizing plate 9 around the hinge 7, thereby applying certain pressure on to the master bag 43.

Figure 12B:
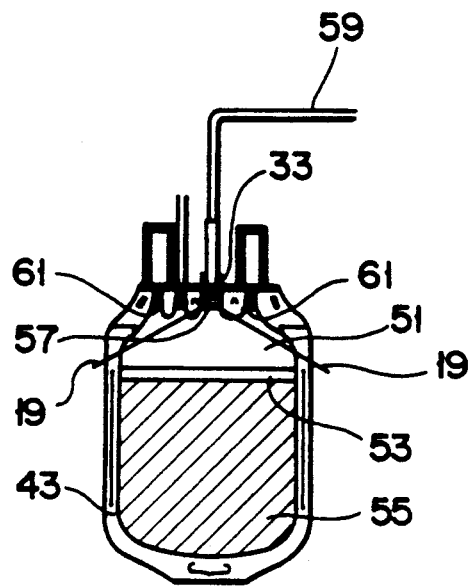

FIG. 12B is a front view of the master bag 43 at the step described above.

As is clear from FIG. 11B and FIG. 12B, in the first cycle of pressing, the upper layer comprising a plasma component 51 is force-flowed out from the liquid transfer port 57, getting transferred through connecting tube 59 into the first sub-bag 45. As a result, the levels of the middle layer 53 comprised of a buffy coat component, and the lower layer 55 composed of a dense erythrocyte component are raised.

As the plasma component 51 is flowed out, the total volume of the blood within the master bag 43 decreases. Therefore, the squeezer means 15 is given ease of squeezing the upper part of the master bag 43, and the pulling force of each spring 27 is applied to the respective arm portions 19 of the squeezer means 15. As a result, the arm portions 19 becomes workable to squeeze the liquid storage chamber, with the respective inner walls of the liquid storage chamber getting in closer contact with each other, whereby a passage is formed, which will become narrower the toward the liquid transfer port 57.

Figure 12C:
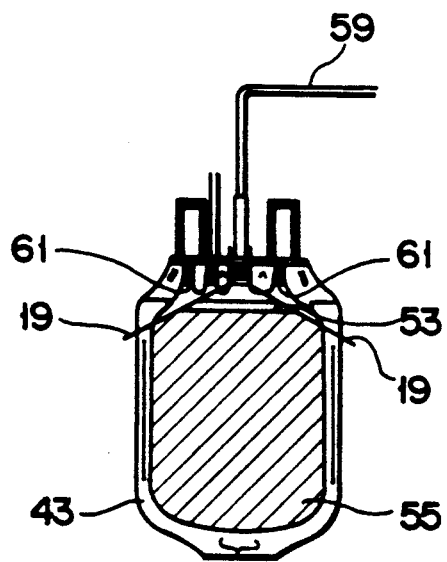

Further thrusting the pressurizing plate 9, the top level of the buffy coat component 53 is raised up to the upper end of the master bag, as shown in FIG. 12C.

Further thrusting the pressurizing plate 9 entails force-transferring the plasma component 51 still remaining in the master bag 43, the buffy coat component 53, and a part of the dense erythrocyte component 55 into the second sub-bag 47 via the connecting tube 59 from the liquid transfer port 57.

At this stage, as described in the foregoing, the respective inner walls of the liquid storage chamber are already in close contact with each other, except for the liquid transfer port 57. As a result, a passage is formed, the width of which gets narrower toward the liquid transfer port 57, with a liquid drain port 61 of the master bag 43 kept off from said passage.

The result is that the buffy coat component 53 to be transferred to the exterior is allowed to completely flow out without getting into said liquid drain port 61 and subsequent staying there.

Figure 12D:
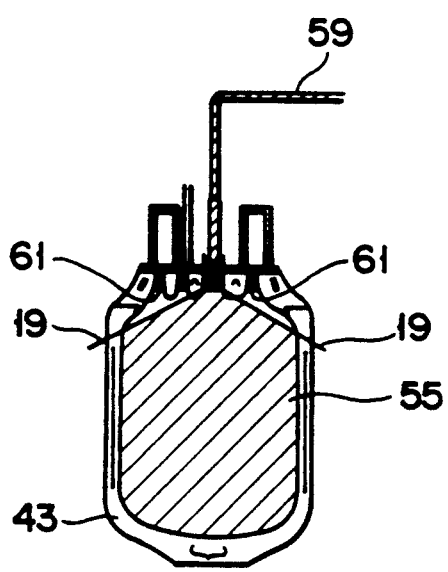

FIG. 12D is an illustrative diagram showing a condition of the master bag after the buffy coat component 53 is transferred outside. As shown in the figure, only dense erythrocyte component is left in the master bag 43.

The buffy coat component 53 transferred into the second sub-bag 47 goes through a process of centrifugal separation. Then, a dense platelet component fractionated by the centrifugal separation is transferred into the third sub-bag 49, resulting in completion of the blood component separating process.

In the embodiment referred to above, the squeezer means 15 is described to be of such a configuration wherein the squeezer means is an integral part of the liquid component separator 1 which is coupled to the retainer plate 5. But the squeezer means 15 can otherwise manufactured to be of an independent piece which is designed mountable to and dismountable from the retainer plate 5.

Presented in each of FIGS. 13A and 13B is one embodiment of the squeezer means 15 designed to be of a mountable/dismountable independent piece.

A squeezer means 62 of such a design described above is provided with a support 65, arm portions 19 which are coupled to the support 65 by way of hinges 63, a hook 31 arranged at the left end of one said arm portion 19, and the lock 29 which is arranged at the right end of said support 65 and is engageable with the hook 31.

The squeezer means 62 is put to use, following the procedure below. First, the flexible container is set to the retainer plate 5. The squeezer means 62 is then positioned to the upper part of the retainer plate 5, keeping the squeezer means 62 released open as shown in FIG. 13A. Subsequently, said squeezer means 62 is closed by being turned around the respective hinges 63. Finally, the squeezer means 62 is fixed by engaging the hook 31 with the lock 29 as shown in FIG. 13B.

The subsequent steps to be taken is as the same as those for the preceding embodiment.

It should be noted that the squeezer means 62 is not limited to the above configuration, but is allowed to be of variously optional configurations.

Though the description in the foregoing is for the case where the flexible container has the liquid transfer port located at its upper part, it should also be kept in mind that the liquid transfer port can be provided at the lower part of the flexible container.

Further, although the present invention has been described in the case where a blood bag is used for the flexible container, the liquid component separator according to the present invention is also applicable to liquid containers for industrial-use.

As is apparent form the forgoing description, the present invention coincides with a method of liquid component separation characterized in that the process of liquid component separation referred to above is implemented in a manner that respective inner wall members of a liquid storage chamber will partly be brought into close contact in advance so as to form a passage, the width of which is narrower toward a liquid transfer port, with the liquid transfer port excluded, in a step to separately transfer to the exterior a liquid component on a liquid transfer port side via said liquid transfer port by externally pressing to a flat configuration a flexible container which has said liquid transfer port located either at its upper or lower part, and wherein some liquid is contained while separated in at least an upper and a lower portions.

In addition, the present invention is identical with a liquid component separator characterized in that the liquid component separator is devised for direct use is effecting said method of the present invention, and comprises a retainer means arranged aslant or perpendicularly to hold a soft flexible container which has a liquid transfer port located either at its upper or lower part, a pressurizing means arranged opposite to said retainer means to externally press said soft flexible container to a flat configuration while firmly holding same between said retainer means and said pressurizing means and a squeezer means arranged on the liquid transfer port side of said flexible container set to said retainer means to squeeze said liquid transfer port side of said flexible container so as to partly bring respective inner wall members of a liquid storage chamber into close contact with each other, with said liquid transfer port of said flexible container excluded, in a manner that a passage will be formed, which becomes narrower toward said liquid transfer port.

Further, the present invention comprises a soft flexible container squeezer means characterized in that said flexible container squeezer means provided as a related attachment for direct use in effecting said method of the present invention is furnished with a squeezing member devised to partly bring the respective inner wall members of the soft flexible container into close contact with each other in a manner to form such a passage which becomes narrower with the liquid transfer port side of said flexible container relocating toward said liquid transfer port.

As is described in detail, following effects are obtained according to the present invention, particularly in the case where a master blood bag is used for a flexible bag. In this case, the squeezer means of the liquid component separator applied to the master bag, and the respective inner walls of the master blood bag, except for a liquid transfer port, are brought into close contact with each other, in a manner that there will be formed such a passage which becomes narrower toward the liquid transfer port. Therefore, when the master bag is pressed with a pressurizing plate of the separator according to the present invention, a blood component such as a buffy coat or the like which should be separately transferred into a respective sub-bag is allowed to flow through the passage without getting into a liquid drain port and the like other than the liquid transfer port. As a result, a blood component such as a buffy coat is smoothly transferred into the sub-bag without staying or remaining in the master bag.

As a consequence, it becomes feasible to separate precisely the buffy coat from the dense erythrocytes remaining in the master blood bag, bringing about efficient or sufficient removal of leukocytes.

Further, since the buffy coat is allowed to be transferred from the master blood bag into a the sub-bag with high efficiency, the rate of recovering platelets from the separated buffy coat can likewise be increased.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method for separating liquid components, which liquid components have been fractionated in advance into at least an upper layer liquid component and a lower layer liquid component in a soft flexible container provided with a liquid storage chamber and a liquid transfer port in liquid communication with said storage chamber, said liquid transfer port being located at one of an upper part and a lower part of the flexible container, comprising:

pressing the flexible container to a substantially flat configuration, so as to cause flowing out of at least one of the liquid components from the storage chamber through the liquid transfer port;

one of said upper part and said lower part of the flexible container having said liquid transfer port and also having at least one recess or corner in which said upper and lower layer liquid components can stay;

bringing opposite inner walls of a liquid storage chamber of the flexible container, except for an area in the vicinity of said liquid transfer port, by means of a squeezing means, at least partly into close contact with each other prior to the step of pressing the flexible container to a flat configuration, so as to block off said recess or corner and to form a liquid component flowing passage from which the recess or the corner is excluded, the liquid component flowing passage becoming narrower toward the liquid transfer port and leading to the liquid transfer port.

2. The method according to claim 1, wherein the step of bringing opposite inner walls of the liquid storage chamber at least partly in close contact with each other, comprises pressing portions of one wall of said liquid storage chamber against an opposed wall of said liquid storage chamber by means of said squeezing means, said squeezing means pressing said portions of said one wall against said opposed wall in the area of said at least one recess or corner of said liquid storage chamber and not pressing portions of said one wall against said opposed wall in the vicinity of the liquid transfer port.

3. The method according to claim 2, wherein said step of pressing comprises pressing said portions of said one wall by means of at least one angled arm member to block off said at least one recess or corner.

4. The method according to claim 3, wherein said step of pressing said portions of said one wall comprises pressing portions of said one wall by means of a pair of angled arm members.

5. The method according to claim 4, wherein said step of pressing comprises maintaining a liquid component flowing passage between said opposite inner walls of said liquid storage chamber and between said pair of angled arm members.

6. In a combination of a soft flexible container and a liquid component separator for separating liquid components which have been fractionated in advance into at least an upper layer liquid component and a lower layer liquid component in said soft flexible container, the separator comprising:

retaining means for holding slantingly or upright said flexible container, said flexible container having a liquid storage chamber in which said upper and lower layer liquid components are received, and a liquid transfer port located in one of an upper part and a lower part of said flexible container;

one of said upper part and said lower part of said flexible container, having said liquid transfer port, also having at least one recess or corner in which said upper and lower layer liquid components can stay;

pressurizing means arranged opposite to said retaining means, for enabling holding of said flexible container between said retaining means and said pressurizing means, and for pressing said flexible container against said retaining means into a substantially flat configuration; and squeezer means coupled to said retaining means and arranged so as to be positioned over the liquid transfer port side of the flexible container, the squeezer means being arranged to squeeze the liquid transfer port part of said flexible container held on the retaining means such that opposite inner walls of said liquid storage chamber, except for the area of the liquid transfer port, are at least partly brought into close contact with each other, the squeezer means defining borders of a passage extending from said liquid storage chamber to said liquid transfer port for flowing out of at least one of the liquid components through said liquid transfer port, and blocking off communication between said liquid storage chamber and said at least one recess or corner, such that the passage becomes narrower toward the liquid transfer port and said at least one recess or corner is excluded from the passage.

7. The separator according to claim 6, wherein said squeezer means comprises a squeezing member for pressing portions of one wall of said liquid storage chamber against an opposed wall of said liquid storage chamber in the area of said at least one recess or corner of said liquid storage chamber and not pressing portions of said one wall against said opposed wall in the vicinity of the liquid transfer port.

8. The separator according to claim 7, wherein said squeezing member comprises at least one angled arm member arranged to block off said at least one recess or corner.

9. The separator according to claim 8, wherein said squeezing member comprises at least two angled arm members arranged to block off a respective pair of recesses or corners.

10. The separator according to claim 9, wherein said angled arm members are connected to each other, and include a central portion between said angled arm members which does not press said one wall against said opposed wall in the vicinity of the liquid transfer port.

11. The separator according to claim 9, wherein said squeezing member is pivotally connected to a pressing surface, with said flexible container interposed between said squeezing member and said pressing surface, and means is provided for pressing said squeezing member against said pressing surface to press said flexible container therebetween.

12. The separator according to claim 11, wherein said means for pressing said squeezing member against said pressing surface comprises at least one spring means coupled between said squeezing member and said pressing surface.

13. In a combination of a soft flexible container and a squeezing tool for squeezing the soft flexible container containing liquid components, which have been fractionated in advance into at least an upper layer liquid component and a lower layer liquid component, said soft flexible container having a liquid storage chamber and a liquid transfer port in liquid communication with said storage chamber, said liquid transfer port being for flowing out of at least one of the upper and lower layer liquid components from said storage chamber, and at least one recess or corner in said soft flexible container in which the upper and lower layer liquid components can stay;

the squeezing tool comprising:
a squeezing means for receiving said soft flexible container, said squeezing means being operable to bring opposite inner walls of said soft flexible container, except for an area in the vicinity of the liquid transfer port, into close contact with each other such that a liquid flowing passage is formed, said squeezing means comprising blocking means for blocking said at least one recess or corner from said liquid transfer port and means for defining borders of the liquid flowing passage to extend from said liquid storage chamber to said liquid transfer port and to become narrower toward said liquid transfer port, such that said at least one recess or corner of said soft flexible container is excluded from said liquid flowing passage.

14. The squeezing tool according to claim 13, wherein said blocking means of said squeezing means comprises a squeezing element arranged to press portions of one wall of said liquid storage chamber against an opposed wall of said liquid storage chamber in the area in the vicinity of said at least one recess or corner of said liquid storage chamber, and not to press portions of said one wall against said opposed wall in the vicinity of the liquid transfer port.

15. The squeezing tool according to claim 14, wherein said blocking means comprises at least one angled arm member arranged to block off said at least one recess or corner.

16. The squeezing tool according to claim 15, wherein said blocking means comprises at least two angled arm members arranged to block off a pair of recesses or corners.

17. The squeezing tool according to claim 16, wherein said angled arm members are connected to each other, and include a central portion between said angled arm members which does not press said one wall against said opposed wall in the vicinity of the liquid transfer port.

18. The squeezing tool according to claim 16, wherein said squeezing means is pivotally connected to a pressing surface, with said flexible container interposed between said squeezing means and said pressing surface, and means is provided for pressing said squeezing means against said pressing surface to press said flexible container therebetween.

19. The squeezing tool according to claim 18, wherein said means for pressing said squeezing means against said pressing surface comprises at least one spring means coupled between said squeezing means and said pressing surface.

* * * * *